United States Patent
Verburg

(10) Patent No.: US 10,611,698 B2
(45) Date of Patent: Apr. 7, 2020

(54) EMULSIONS COMPRISING SILICIC ACID

(71) Applicant: Cindro Holding B.V., Twisk (NL)

(72) Inventor: Thomas Hendrik Johannes Verburg, Twisk (NL)

(73) Assignee: Cindro Holding BV, Twisk (NL)

( * ) Notice: Subject to any disclaimer, the term of this patent is extended or adjusted under 35 U.S.C. 154(b) by 457 days.

(21) Appl. No.: 15/261,671

(22) Filed: Sep. 9, 2016

(65) Prior Publication Data

US 2017/0066694 A1    Mar. 9, 2017

(30) Foreign Application Priority Data

Sep. 9, 2015  (NL) ..................................... 1041500

(51) Int. Cl.
| | | |
|---|---|---|
| *A61K 8/25* | (2006.01) | |
| *C05D 9/02* | (2006.01) | |
| *C05G 3/00* | (2020.01) | |
| *C05D 3/00* | (2006.01) | |
| *C05D 5/00* | (2006.01) | |
| *C05C 3/00* | (2006.01) | |
| *A61Q 19/00* | (2006.01) | |
| *A61K 8/90* | (2006.01) | |
| *A61K 8/06* | (2006.01) | |
| *A61K 45/06* | (2006.01) | |
| *A61K 9/113* | (2006.01) | |
| *A61K 33/00* | (2006.01) | |
| *A01N 25/04* | (2006.01) | |
| *A61K 9/107* | (2006.01) | |

(52) U.S. Cl.
CPC ............... *C05D 9/02* (2013.01); *A01N 25/04* (2013.01); *A61K 8/064* (2013.01); *A61K 8/25* (2013.01); *A61K 8/90* (2013.01); *A61K 9/107* (2013.01); *A61K 9/113* (2013.01); *A61K 33/00* (2013.01); *A61K 45/06* (2013.01); *A61Q 19/00* (2013.01); *C05C 3/00* (2013.01); *C05D 3/00* (2013.01); *C05D 5/00* (2013.01); *C05G 3/00* (2013.01); *C05G 3/0064* (2013.01); *A61K 2800/10* (2013.01)

(58) Field of Classification Search
CPC .......... A61K 8/25; A61K 8/062; A61K 8/064; C08K 9/06; C09C 1/30
See application file for complete search history.

(56) References Cited

U.S. PATENT DOCUMENTS

| | | | | |
|---|---|---|---|---|
| 3,632,352 A | * | 1/1972 | Muller | ..................... A23C 1/16 |
| | | | | 426/541 |
| 4,474,912 A | | 10/1984 | Ozmeral et al. | |
| 9,980,489 B2 | * | 5/2018 | Roose | ..................... A01N 59/00 |
| 10,028,895 B2 | * | 7/2018 | Bergeron | ................ A61K 8/062 |
| 2009/0215723 A1 | * | 8/2009 | Le | ........................... A61K 8/585 |
| | | | | 514/63 |
| 2010/0068294 A1 | | 3/2010 | Van Den Berghe | |
| 2011/0038824 A1 | * | 2/2011 | Toyoda | ..................... A61K 8/25 |
| | | | | 424/70.11 |
| 2013/0130902 A1 | * | 5/2013 | Roose | ..................... A01N 59/00 |
| | | | | 504/187 |
| 2014/0341981 A1 | * | 11/2014 | Bergeron | ................ A61K 8/062 |
| | | | | 424/451 |
| 2015/0216766 A1 | * | 8/2015 | Tanaka | ..................... A61Q 17/04 |
| | | | | 424/401 |
| 2017/0066694 A1 | * | 3/2017 | Verburg | ................. A01N 25/04 |

FOREIGN PATENT DOCUMENTS

| | | |
|---|---|---|
| JP | H05287153 A | 11/1993 |
| WO | WO1995021124 A1 | 8/1995 |
| WO | WO2006136003 A1 | 12/2006 |
| WO | WO2011120872 A2 | 10/2011 |

OTHER PUBLICATIONS

Database WPI Week 199348 Thomson Scientific, London, GB; AN 1993-383212 XP002756488 & JP H05 287153 (Daicel Chem Ind Ltd), Nov. 2, 1993.
European Patent Office, International Search Report, Application No. NL 1041500, dated Apr. 25, 2016, European Patent Office, Rijswijk, Netherlands.
Allen, K.A. and W.J. McDowell, Emulsion Stabilization by Silicic Acid, ORNL-2771, Oak Ridge National Laboratory, Chemical Technology Division, Oak Ridge, TN, Aug. 17, 1959, pp. 1-15.
Iler, Ralph K., The Chemistry of Silica, John Wiley & Sons, Inc., New York, NY, Jun. 6, 1979, pp. 5, 179, 323-327.
Kibbe, Arthur H. (ed.), Poloxamer, Handbook of Pharmaceutical Excipients, 2000, pp. 386-388, Third Edition, Pharmaceutical Press, London (XP002398334).

* cited by examiner

*Primary Examiner* — Michael A Salvitti
(74) *Attorney, Agent, or Firm* — Thomas P. O'Connell; O'Connell Law Firm

(57) ABSTRACT

An emulsion of water and oil comprising a solution of silicic acid and one or more stabilizing compounds in water, and one or more block copolymers as emulsifiers. Aside from water-in-oil and oil-in-water emulsions, the invention also offers co-emulsions of water with silicic acid in oil in water, water in oil in silicic acid with water, and oil in water with silicic acid in oil. Aside from silicic acid, the emulsion or co-emulsion preferably comprises one or more other, oil-soluble and/or water-soluble, active ingredients.

The stable emulsions with silicic acid according to the invention can be favorably used for medical or cosmetic purposes, as dietary supplements, liquid fertilizers, crop protection agents, biocides, biostimulants, plant nutrients, soil improvers, catalyzers, antioxidants, or household products.

21 Claims, No Drawings

EMULSIONS COMPRISING SILICIC ACID

FIELD OF THE INVENTION

The invention relates to an emulsion of water and oil. The invention further relates to a method of preparing such an emulsion, and the uses thereof.

BACKGROUND OF THE INVENTION

There is great need for silicic acid in stable form, since silicic acid is used as an active ingredient for living organisms, such as humans, animals, plants, and aquatic organisms, for very broad purposes, such as:
  maintenance of strong and healthy bones, skin, hair, nails;
  synergy with other active ingredients;
  distribution of other active ingredients throughout bodies;
  as an antioxidant for heavy metals;
  against biotic and abiotic stress;
  for promoting growth.

Silicon is a common mineral found in the Earth's crust. Because of its high affinity for oxygen, silicon reacts with oxygen to form silicon dioxide and silicates, which are the most common types of soil minerals. Since these forms of silicon are highly stable, they do not rapidly degrade in the biological system, which is why soluble and biologically absorbable silicon is found in very low concentrations in nature.

Silicic acid is a general name for the family of silicon compounds $SiO_2.nH_2O$, as in n=2 $Si(OH)_4$ in basic solution. Soluble and biologically absorbable silicon is found in very low concentrations in nature, at pH levels of <9 under 2 mM predominantly in the form of monomeric silicic acid; above 2 mM, polymerization occurs. However, a concentration of 2 mM is too low for using this substance as an additional source of nutrition in the form of, for instance, dietary supplements. Therefore, a higher concentration of monomeric silicic acid, which can be prepared by chemical synthesis, is desired. A highly concentrated solution of silicic acid, however, needs to be stabilized to prevent the particles from growing into poorly soluble and poorly biologically absorbable silicon compounds. The Chemistry of Silica (1979) on pages 323 through 328 describes the stabilization process—by means of, amongst other things, steric stabilization (in which process a nonionic polymer, such as polyethylene glycol, is adsorbed to the surfaces of silicic acid molecules) and polar compounds such as, for instance, quaternary ammonium salts (like carnitine, betaine, and choline)—to prevent polymerization.

There are various known synthesis reactions that can be used for the industrial production of silicic acid. Two known synthesis reactions have been described in The Chemistry of Silica (1979), on pages 5 and 179:
  acid-base reaction with (sodium) silicate and hydrochloric acid; and
  hydrolysis of silicon tetrachloride.

In the synthesis of silicic acid, it is almost impossible to obtain 100% monomeric silicic acid. Monomeric silicic acid does not, or only very weakly, react with metals, but larger silicic acid compounds such as dimers, trimers, oligomers, polymers, and colloids, which are always present after silicic acid synthesis, react more strongly.

The affinity of silicic acid for other ingredients in aqueous solutions poses several problems: phosphorus and boron react with silicic acid to form Si—O—P (silicon phosphate) and Si—O—B (silicon borate) compounds; in low-pH aqueous solutions, monomeric silicic acid stimulates the oxidation of $Fe^{2+}$ into $Fe^{3+}$ and forms a complex with $SiO_2.nH_2O$. Calcium and magnesium form complexes with silicic acid as well, and molybdenum forms into the silicomolybdate complex.

Since silicic acid reacts with other ingredients, and complexes of silicic acid with additional active ingredients are unwanted in dietary supplements, liquid fertilizers, medications, cosmetic products, et cetera, it is necessary to isolate the silicic acid from other active ingredients in order to prevent interaction.

DETAILED DESCRIPTION OF PREFERRED EMBODIMENTS

The present invention aims to offer a silicic acid solution that does not show any gelation, remains stable over a long period of time, does not react with other compounds, and that can, therefore, be used for medical or cosmetic purposes, or for dietary supplementation.

To achieve the intended goal, the invention offers an emulsion of the preamble, comprising a solution of silicic acid, one or more stabilizing compounds in water, and one or more block copolymers as emulsifying agents; preferably one or more W/O or O/W block copolymers comprising two or more structural units selected from:
  nonionic structural units selected from the group consisting of: alkylene such as 1-12 C alkylene, in particular methylene, ethylene, propylene, and butylene, 1-12 C alkylene oxide such as ethylene oxide, propylene oxide, and butylene oxide, glycol, styrene, pyrrole, tetrahydrofuran, glycolide, butadiene, isoprene, ethylene-ran-butylene, glycerol, amine-comprising units such as ethylenimine and ethanediamine, sorbitol, alkylphenol, alkanol such as 1-12C alkanol, in particular methanol, ethanol, propanol, butanol, and isotridecanol, ether such as 1-12 C alkyl ether, in particular methyl, ethyl, propyl, and butyl ether, cetyl, lauryl, oleyl, and stearyl ether, phenol, in particular alkylphenol such as 1-12 C alkyl, preferably nonylphenol, sarcosine such as oleoyl sarcosine, lanolin, lactide, caprolactone, castor oil and amino acid; ionic structural units selected from the group consisting of: acrylic acid, acrylate, methacrylic acid, methacrylate, propoxylate such as glycerol propoxylate, taurate such as sodium-N-methyl oleoyl taurate, stearate such as sorbitol stearate, sorbitol oleate, laurate such as sorbitol laurate, sulfonate such as ammonium dodecylbenzenesulfonate, sulfate such as calcium alkylarylsulfate or ethyldimoniumethosulfate, in particular talc ethyldimonium ethosulfate and phosphate such as trialkylphosphate, in particular tridecyl phosphate.

Examples of nonionic W/O or O/W copolymers according to the invention are polyalkyleneoxide block copolymers, block copolymers of polyethylene glycol and polypropylene glycol, and polylactic-co-glycolic acid (PGLA), polystyrene-block-poly(ethylene-ran-butylene)-block-polysterene, and nonionic surfactants in the form of block polymers.

Examples of ionic W/O or O/W block copolymers according to the invention are the diblock copolymers of styrene and methylmethacrylate and anionic surfactants in the form of block polymers.

In a special embodiment, the emulsion comprises one or more active ingredients aside from silicic acid. In particular, the silicic acid solution has a pH level of 0-12, preferably 0-9, more preferably 0-7, most preferably 0-5, and with utmost preference 0-2.

The stabilizing compounds preferably have electrostatic or steric properties. The stabilizing compounds with electrostatic properties are preferably polar compounds, more preferably quaternary ammonium salts such as trialkylhydroxyalkylammonium compounds, for instance one or more selected from the group consisting of choline, carnitine and betaine and salts thereof. Stabilizing compounds with steric properties are preferably hydrogen-adsorbing agents such as one or more selected from the group consisting of polysorbate, vegetable gum, cellulose, polyglycerol esters, polyethylene glycol, dextrose, propylene glycol, pectin and sugars.

In particular, the invention offers an emulsion according to the invention whereby the solution of silicic acid in water has been emulsified into the oil with one or more W/O block copolymers to form a W/O (water-in-oil) emulsion. Said one or more W/O block copolymers are preferably selected from the group described above.

The invention also offers an emulsion according to the invention whereby the oil has been emulsified into the solution of silicic acid in water with one or more O/W block copolymers to form an O/W (oil-in-water) emulsion. Said one or more O/W block copolymers are preferably selected from the group described above.

The invention further offers an emulsion according to the invention whereby the W/O emulsion has been emulsified into water without silicic acid to form a Wsi/O/W emulsion (complex or co-emulsion of a water-with-silicic-acid-in-oil emulsion, in water emulsion). In particular, the water without silicic acid in the Wsi/O/W emulsion comprises water-soluble active ingredients. Preferably, such water-soluble active ingredients are selected from one or more of the water-soluble salts of potassium, calcium, magnesium, iron, copper, manganese, molybdenum, boron, and hydrophilic/lipophilic active ingredients such as water-soluble compounds of vitamins, minerals, microorganisms, plant extracts, algae, fatty acids, pharmaceuticals, crop protection agents, biocides, enzymes, hormones, and cosmetic active ingredients. The water phase with silicic acid in a co-emulsion with two water phases is referred to as Wsi in this present application.

Furthermore, the invention offers an emulsion whereby the O/W emulsion according to the invention has been emulsified into oil as a O/W/O emulsion, a so-called O/W/O co-emulsion, with two oil phases. In particular, the oil comprises, or optionally both oil phases comprise, oil-soluble active ingredients, preferably one or more selected from the group consisting of zinc oxide, calcium borate, manganese carbonate, magnesium carbonate, magnesium hydroxide, ammonium molybdate and hydrophobic active ingredients such as oil-soluble compounds of vitamins, minerals, microorganisms, plant extracts, algae, fatty acids, pharmaceuticals, crop protection agents, biocides, enzymes, hormones and cosmetic active ingredients.

Preferably, one or each oil phase of the emulsion according to the invention is selected from the group consisting of vegetable oils, animal oils, also including fish oil, ethereal oils and essential oils.

Depending on its use, one or each oil phase of the emulsion according to the invention may be, for instance, a vegetable oil as selected from one or more of almond oil, argan oil, avocado oil, ben oil, borage oil, cocoa butter, grapeseed oil, hazelnut oil, hemp oil, jatropha oil, cottonseed oil, coconut oil, andiroba oil, flaxseed oil, macadamia nut oil, corn oil, olive oil, palm oil, palm kernel oil, peanut oil, rapeseed oil, rice bran oil, sacha inchi oil, safflower oil, sesame oil, soybean oil, wheat bran oil, evening primrose oil, walnut oil, castor oil, sunflower oil, cannabidiol (CBD) oil, and cannabis oil.

For emulsions intended for 'green' crop protection agents, one or each oil phase is preferably an essential oil as selected from one or more of oils made of lemon grass (*Cymbopogon citratus*), *Eucalyptus globulus*, rosemary (*Rosmarinus officinalis*), vetiver (*Vetiveria zizanioides*), clove buds (*Eugenia caryophyllata*) and thyme (*Thymus vulgaris*), peppermint (*Mentha piperita*), pennyroyal (*Mentha pulegium*), spearmint (*Mentha spicata*), basilicum (*Ocimum basilicum*), *Artemesia vulgaris, Melaleuca leucadendron, Pelargonium roseum, Lavandula angustifolia, Juniperus virginiana, Cinnamomum zeylanicum, Lavandula angustifolia* syn. *L. officinalis, Tanacetum vulgare, Rabdosia melissoides, Acorns calamus, Eugenia caryophyllata, Ocimum* species, *Gaultheria procumbens, Cuminum cymimum, Bunium persicum, Trachyspermum ammi, Foeniculum vulgare, Abelmoschus moschatus, Cedrus* species, *Piper* species, citronella (*Cymbopogon nardus, Cimbopogon winteriana*), lemon (*Citrus limonum*), rose (*Rosa damascena*), lavender, vetiver (*Vetiveria zizanioides*), catnip (*Nepeta cateria*), *Trachyspermum* species, *Ocimum sanctum, Satureja hortensis, Thymus serpyllum, Origanum creticum, Ageratum conyzoides, Aegle marmelos*, dill oil (dill plant [*Anethum sowa*]), dillapiole, *Anethum graveolens*, spearmint oil (*Mentha spicata*), *Curcuma longa*, cucumber and ginger oil, neem oil.

For emulsions intended for cosmetics, one or each oil phase is preferably an ethereal oil as selected from one or more oils made of *Pimpinella anisum, Ocimum basilicum, Citrus bergamia, Betula lenta, Satureja hortensis, Artemisia vulgaris, Juniperus virginiana, Cupressus sempervirens, Citrus limonum, Cymbopogon nardus, Pinus sylvestris, Anethum graveolens, Eucalyptus globulus, Zingiber officinale*, (Geranium) *Pelargonium odorantissimum*, hyssop (*Hyssopus officinalis*), St. John's wort (*Hypericum perforatum*), juniper (*Juniperus communis*), cajeput (*Melaleuca leucadendron*), camphor (*Camphora officinarum*), chamomile (*Matricaria chamomilla*), cinnamon (*Cinnamomum zeylanicum*), cardamon (*Elletaria cardamomum*), coriander (*Coriandrum sativum*), clove buds (*Syzygium oromaticum*), bay laurel (*Laurus nobilis*), lavender (*Lavandula officinalis*), lemongrass (*Cymbopogon citratus*), lime (*Citrus aurantifolia*), mandarin orange (*Citrus reticulata*), marjoram (*Origanum majorana*), myrrh (*Commiphora myrrha*), myrtle (*Myrtus communis*), broad-leaved paperbark (*Melaleuca viridiflora*), nutmeg (*Myristica fragrans*), oregano (*Origanum vulgare*), palmarosa (*Cymbopogon martini motia*), patchouli (*Pogostemon patchouli*), peppermint (*Mentha piperita*), rosewood (*Aniba rosaeodora*), rosemary (*Rosmarinus officinalis*), sage (*Salvia officinalis*), sandalwood (*Santalum album*), Sassafras (*Sassafras officinalis*), clary (*Salvia sclarea*), orange (*Citrus aurantium dulcis*), tea tree (*Melaleuca alternifolia*), turpentine (*Pinus resin, Pinus pinaster*), thyme (*Thymus vulgaris*), fennel (*Foeniculum vulgare*), vetiver (*Vetiveria zizanioides*), frankincense (*Boswellia carterii*), carrot seeds (*Daucus corota*), Ylang-Ylang (*Cananga odorata*), silver fir (*Abies alba*), black pepper (*Piper nigrum*).

Active ingredients in oils that can be used in particular in emulsions with one or more oil phases according to the invention are: terpenes (hydrocarbons) such as myrcene, pinene, terpinene, limonene, p-cymene, α-en β-phellandrene et cetera, terpenoids (oxygen-containing hydrocarbons) such as acyclic monoterpene alcohols (geraniol, linalool), monocyclic alcohols (menthol, 4-carvomenthenol, terpineol, carveol, borneol), aliphatic aldehydes (citral, citronellal, perillaldehyde), aromatic phenols (carvacrol, thymol, safrole, eugenol), bicyclic alcohol (verbenol), monocyclic ketones (menthone, pulegone, carvone), bicyclic monoterpene ketones (thujone, verbenone, fenchone), acids (citronellic acid, cinnamic acid), esters (linalyl acetate), oxides (1,8- cineole), sulphur-containing composites, methylantranilate, coumarins, or sesquiterpenes (C15)).

Furthermore, the invention offers an emulsion whereby an emulsion of a solution of water with optionally one or more active ingredients as selected from the group consisting of water-soluble salts of potassium, calcium, magnesium, iron, copper, manganese, molybdenum, boron and hydrophilic/lipophilic active ingredients such as water-soluble compounds of vitamins, minerals, microorganisms, plant extracts, algae, fatty acids, pharmaceuticals, crop protection agents, biocides, enzymes, cosmetic active ingredients, in oil with optionally one or more active ingredients as selected from the group consisting of zinc oxide, calcium borate, manganese carbonate, magnesium carbonate, magnesium hydroxide, ammonium molybdate, hydrophobic active ingredients such as oil-soluble compounds of vitamins, minerals, microorganisms, plant extracts, algae, fatty acids, pharmaceuticals, crop protection agents, biocides, enzymes, and cosmetic active ingredients, has been emulsified into a solution of silicic acid in water to form a W/O/W emulsion, a so-called W/O/Wsi emulsion.

Preferably, the emulsion or co-emulsion according to the invention comprises a solution of silicic acid in water with a silicon concentration of at least 0.001% by weight, preferably between 0.001 and 10.000% by weight, more preferably between 0.01 and 5.000% by weight, and most preferably between 0.1 and 3.000% by weight. The solution of silicic acid in water in the emulsion or co-emulsion according to the invention has a volume concentration of stabilizing ingredients of preferably 1-95%, more preferably 10-70%, most preferably 20-60%.

A further aspect of the present invention relates to a method of preparing a W/O emulsion or an O/W emulsion according to the invention, whereby:
  one or more active ingredients as selected from the group consisting of zinc oxide, calcium borate, manganese carbonate, magnesium carbonate, magnesium hydroxide, ammonium molybdate, hydrophobic active ingredients such as oil-soluble compounds of vitamins, minerals, microorganisms, plant extracts, algae, fatty acids, pharmaceuticals, crop protection agents, biocides, enzymes, cosmetic active ingredients and surface active agents that stabilize the active ingredients in oil, such as for instance nonionic block copolymers, polyester/polyamine condensation polymers, polymeric dispersants, are added to oil, forming the oil phase;
  silicic acid is produced in water by means of an acid-base reaction of a silicon compound with a strong acid, or by means of hydrolysis of silicon compounds in the form of salts such as halogenides, for instance silicon tetrachloride, esters, rocks such as quartz or flint, or acyl group derivatives such as silicon tetraacetate, after which the silicic acid produced is preferably purified by means of ion exchange,
  and to the water phase thus created are added surface active agents and stabilizing ingredients up to a volume concentration of said stabilizing ingredients of preferably 1-95%, more preferably 10-70%, most preferably 20-60%;
  for a W/O emulsion one or more W/O block copolymers are added to the oil phase and the water phase is emulsified into the oil phase, and for an O/W emulsion one or more O/W block copolymers are added to the water phase and the oil phase is emulsified into the water phase, with
    the optional addition of surface active agents, additives, binding agents, thickening agents, anti-foaming agents, aromatics, colorants, and/or flavorings to the W/O or O/W forming emulsion.

Furthermore, the present invention offers a method of preparing a Wsi/O/W emulsion according to the invention, whereby the W/O emulsion formed according to the method described above is emulsified into water without silicic acid with optionally one or more active ingredients as selected from the group consisting of water-soluble salts of potassium, calcium, magnesium, iron, copper, manganese, molybdenum, boron and hydrophilic/lipophilic active ingredients such as water-soluble compounds of vitamins, minerals, microorganisms, plant extracts, algae, fatty acids, pharmaceuticals, crop protection agents, biocides, enzymes, cosmetic active ingredients, and whereby optionally surface active agents, additives, binding agents, thickening agents, anti-foaming agents, aromatics, colorants, and/or flavorings to the Wsi/O/W forming emulsion are added to the Wsi/O/W forming emulsion.

The invention also offers a method of preparing an O/W/O emulsion according to the invention, whereby the O/W emulsion formed according to the method described above is emulsified into oil with optionally one or more active ingredients selected from the group consisting of zinc oxide, calcium borate, manganese carbonate, magnesium carbonate, magnesium hydroxide and ammonium molybdate, and whereby optionally surface active agents, additives, binding agents, thickening agents, anti-foaming agents, aromatics, colorants and/or flavorings are added to the O/W/O forming emulsion.

Another aspect of the invention is the use of one or more of the emulsions according to the invention for medical or cosmetic purposes, as dietary supplements, liquid fertilizers, crop protection agents, biocides, biostimulants, plant nutrients, soil improvers, catalyzers, antioxidants, or household products such as dermatological products or perfumes.

The emulsions and co-emulsions according to the invention optionally also contain other surface-active agents aside from block copolymers, and, further, additives, binding agents, thickening agents, aromatics, colorants and/or flavorings.

In the present application, the term 'block copolymer' is meant to refer to a copolymer whose polymer chains are composed of consecutive segments or "blocks" of two or more distinct polymers. A block copolymer consisting of one block of a polymer A coupled with another block of a second polymer B, is referred to as a diblock A-B. A triblock consists of three blocks, which can be A-B-A or B-A-B. Multiblock copolymers can consist of alternating blocks (A-B)n, (A-B-C)n, et cetera, but many other arrangements are possible. The polymers A, B, C . . . can be either homopolymers or copolymers.

With block copolymers, polymers can be obtained that combine the properties of the individual polymers in a well-defined manner. For instance, a surface-active polymer can be obtained if block A is hydrophobic and block B is hydrophilic. The various types of constituent polymers, their relative proportions, and their specific molecular weights together produce the characteristic properties of a block copolymer. For this reason, one block polymer may be more suitable for a W/O emulsion, whereas another may be more suitable for an O/W emulsion.

In the present application, the term 'active ingredient' is meant to refer to any and all active ingredients except silicic acid. The terms 'active ingredient' and 'silicic acid' are meant to refer to biologically available forms of such compounds, meaning forms that in any way show activity in or on humans, animal, plants, aquatic organisms, insects, or microorganisms. Further, in this patent application the phrasing 'emulsified in . . . to form a . . . emulsion' is meant to refer to the formed emulsion itself. The term 'silicic acid' in this application is meant to refer to monomeric silicic acid, being Si(OH)4, also referred to as orthosilicic acid, monosilicic acid, silicon tetrahydroxide, or tetrahydroxysilane, which molecule can be identified using the beta silicomolybdate method as described in The Chemistry of Silica on page 97. The terms 'multiple emulsion' and 'co-emulsion' are both used to describe an emulsion in an extra liquid phase, whereby the umbrella term 'emulsion' also refers to multiple emulsions and co-emulsions, where applicable. Furthermore, listings introduced by the phrase 'selected from one or more of items where under a group of items', are meant to cover any and all possible combinations, i.e. one or more of any of the items listed, optionally combined with one or more of the items of that group, and vice versa. Where a co-emulsion with two water phases is referred to, the marking 'si' denotes the water phase that contains dissolved silicic acid. It will be evident that in the emulsions according to the invention, silicic acid is invariably present in the water phase.

A paper by K. A. Allen and W. J. McDowell (see http://web.ornl.gov/info/reports/1959/3445603613999.pdf, Emulsion stabilisation by silicic acid, ORNL-2771, Chemical Technology Division [1959]), describes a water-in-oil (W/O) emulsion with silicic acid in oil with a secondary amine. In this emulsion, silicic acid is used for stabilization, but has not been stabilized itself. Moreover, the silicic acid in this emulsion will form a gel that is not absorbable for organisms, and therefore not biologically available.

The emulsion according to the invention offers a satisfactory solution for a long-standing problem: providing a stable solution of silicic acid, a compound with important active properties, optionally combined with other active ingredients. The invention is based on mixtures of simple and multiple emulsions or co-emulsions, whereby the various droplets of the distinct phases contain either silicic acid or other active ingredients. In this manner, each active ingredient retains its own identity. Active ingredients other than silicic acid, which, however, could also interact negatively, can remain isolated from each other within the discrete droplets of multiple emulsions. In an O/W emulsion according to the invention, the oil, which optionally contains dissolved active ingredients, is present in droplets in the water phase, in which silicic acid has been dissolved. In a W/O emulsion according to the invention, the water phase, in which silicic acid has been dissolved, is present in droplets in the oil phase, in which optionally active ingredients have been dissolved. In co-emulsions, diverse active ingredients may have been dissolved into the two water or oil phases, with always at least one of the water phases containing dissolved silicic acid.

For product registrations of, for instance, dietary supplements or liquid fertilizers, and certainly for uses in the medical sector, it is of great importance to know the exact identity of each active ingredient. Silicic acid often combines with other active ingredients in aqueous solutions to form highly complex compounds, in which case the exact nature of the silicon compound cannot be identified by means of common detection methods, but loss of the $Si(OH)_4$ structure under the influence of Ca, Mg, B, P, Al, Mo, Fe, or Ur ions (partial or complete loss, depending on concentrations) and 'conversion' into a complex cannot be prevented. This may lead to inaccuracies in filed product registrations, which in turn may lead to scenarios that conflict with legislation. Authorities need to be aware of the exact identities of substances to which the people, animals, aquatic organisms, and nature are exposed. For this problem, too, the stable silicon emulsions according to the invention offer a solution.

Especially when using one or more of the emulsions for medical or cosmetic purposes, as dietary supplements or as liquid fertilizers, the various emulsions and co-emulsions according to the invention need to comprise very pure silicic acid. Purification of silicic acid to remove heavy metals, such as aluminum, can be achieved by means of separation techniques such as filtration, reverse osmosis, and ion exchange.

The invention is illustrated with the following example.

Preparation W/O Emulsion of Silicic Acid

Step 1. Preparation of a 100% Monomeric Silicic Acid Solution "Liquid A":

Fill tank #1 with 15.00 kg of $H_2O$ and slowly add 5.00 kg of polyethylene glycol 400, and mix for 30 minutes. Then add 2.50 kg of HCl 37% while stirring. Fill tank #2 with 22.50 kg of $H_2O$ and 10.00 kg of $K_2SiO_3$, and mix for 60 minutes. Then add the contents of tank #2 dropwise to tank #1 while stirring.

Subsequently, while stirring, slowly add 40.00 kg of polyethylene glycol 400 to tank #1 and lower its pH level to <1 by dropwise adding 5.00 kg of HCl 37%. Mixing takes place at room temperature.

The resulting liquid is a stable, colorless, transparent solution with a silicon content of 1.2%. Using the 'beta silicomolybdate method' according to the description on page 97 of The Chemistry of Silica (1979), 100% silicic acid in monomeric form is measured (complete reaction within two minutes). This product is referred to as liquid A.

Step 2. Preparation W/O Emulsion:

Pour 1,000 mL of vegetable oil and 1,000 mL of liquid A into a 2,500 mL measuring beaker. Add 100 mL of nonionic block copolymer with a hydrophilic-lipophilic balance (HLB) value of 6, and mix at high speed for 2-10 minutes using an ultrasonic mixer. The resulting emulsion is milky and will remain stable for at least a week. This emulsion can be used directly, for instance for nebulizing as a synergistic product with other active ingredients to develop or protect crops.

While hereinabove the invention has been illustrated with some simple and multiple emulsions and with an example, it will be evident that the invention is in no way limited to said emulsions and example. On the contrary, within the framework of the invention, the average professional will be able to come up with many variations.

What is claimed as deserving the protection of Letters Patent:

1. An emulsion of water and oil comprising a solution of monomeric silicic acid with a pH level of 0-5 and one or more stabilizing compounds in water, and one or more block copolymers as emulsifying agents.

2. An emulsion according to claim 1 further comprising one or more active ingredients selected from the group consisting of water-soluble salts of potassium, calcium, magnesium, iron, copper, manganese, molybdenum, boron; hydrophilic/lipophilic active ingredients consisting of water-soluble compounds of vitamins, minerals, microorganisms, plant extracts, algae, fatty acids, pharmaceuticals, crop protection agents, biocides, enzymes, hormones, and cosmetics; and/or oil-soluble active ingredients selected from the group consisting of zinc oxide, calcium borate, manganese carbonate, magnesium carbonate, magnesium hydroxide, ammonium molybdate and oil-soluble compounds of vitamins, minerals, microorganisms, plant extracts, algae, fatty acids, pharmaceuticals, crop protection agents, biocides, enzymes, hormones, and cosmetics.

3. An emulsion according to claim 1 wherein the one or more stabilizing compounds comprise polar compounds or hydrogen-adsorbing agents.

4. An emulsion according to claim 3 wherein the stabilizing compounds comprise polar compounds.

5. An emulsion according to claim 4 wherein at least one of the stabilizing compounds are quaternary ammonium salts.

6. An emulsion according to claim 3 wherein the stabilizing compounds are hydrogen adsorbing agents wherein at least one of the stabilizing compounds is selected from the group consisting of polysorbate, vegetable gum, cellulose, polyglycerol esters, polyethylene glycol, dextrose, propylene glycol, pectin and sugars.

7. An emulsion according to claim 1 wherein the oil has been emulsified into the solution of monomeric silicic acid in water with one or more O/W block copolymers to form an O/W emulsion.

8. An emulsion according to claim 1 wherein the solution of monomeric silicic acid has been emulsified into the oil with one or more W/O block copolymers to form a W/O emulsion.

9. An emulsion wherein the W/O emulsion of claim 8 is emulsified into water without silicic acid to form a Wsi/O/W emulsion.

10. An emulsion according to claim 9 wherein the water without silicic acid in the Wsi/O/W emulsion comprises one or more water-soluble active ingredients.

11. An emulsion according to claim 10 wherein at least one of the one or more water-soluble active ingredients is selected from the group consisting of water-soluble salts of potassium, calcium, magnesium, iron, copper, manganese, molybdenum, boron and hydrophilic/lipophilic active ingredients.

12. An emulsion according to claim 1 wherein the oil is emulsified into the solution of monomeric silicic acid in water with one or more O/W block copolymers to form an O/W emulsion and wherein the O/W emulsion is emulsified into oil to form an O/W/O emulsion with two oil phases.

13. An emulsion according to claim 12 wherein at least one of the oil phases comprises one or more oil-soluble active ingredients.

14. An emulsion according to claim 13 wherein at least one of the one or more oil-soluble active ingredients is selected from the group consisting of zinc oxide, calcium borate, manganese carbonate, magnesium carbonate, magnesium hydroxide, ammonium molybdate and hydrophobic active ingredients.

15. An emulsion according to claim 12 wherein at least one of the oil phases is selected from the group consisting of vegetable, animal, ethereal and essential oils.

16. An emulsion according to claim 1 wherein an emulsion of a solution of water with one or more active ingredients selected from the group consisting of water-soluble salts of potassium, calcium, magnesium, iron, copper, manganese, molybdenum, boron and hydrophilic/lipophilic active ingredients, in oil with one or more oil-soluble active ingredients selected from the group consisting of zinc oxide, calcium borate, manganese carbonate, magnesium carbonate, magnesium hydroxide, ammonium molybdate and hydrophobic active ingredients is emulsified into a solution of silicic acid in water to form a W/O/Wsi emulsion.

17. An emulsion according to claim 1 wherein the solution of monomeric silicic acid in water has a silicon concentration of at least 0.001% by weight.

18. An emulsion according to claim 1 wherein the solution of monomeric silicic acid in water has a 1-95% volume concentration of stabilizing substances.

19. A method of preparing an emulsion according to claim 1 wherein the oil has been emulsified into the solution of silicic acid in water with one or more O/W block copolymers to form an O/W emulsion or wherein the solution of silicic acid has been emulsified into the oil with one or more W/O block copolymers to form a W/O emulsion, the method comprising the following steps:
   adding one or more active ingredients selected from the group consisting of zinc oxide, calcium borate, manganese carbonate, magnesium carbonate, magnesium hydroxide, ammonium molybdate, hydrophobic active ingredients and surface active agents that stabilize the active ingredients in oil to oil, thus forming an oil phase;
   producing silicic acid in water by an acid-base reaction of a silicon compound with a strong acid or hydrolysis of silicon compounds in the form of salts thus forming a water phase;
   adding to the water phase thus created surface active agents and stabilizing substances up to a volume concentration of the stabilizing substances of 1-95%;
   purifying the silicic acid by ion exchange; and for a W/O emulsion,
   adding one or more W/O block copolymers to the oil phase and emulsifying the water phase into the oil phase; for an O/W emulsion, adding one or more O/W block copolymers to the water phase and emulsifying the oil phase into the water phase.

20. The method of preparing an emulsion wherein the W/O emulsion of claim 19 is further emulsified into water without silicic acid comprising one or more active ingredients selected from the group consisting of water-soluble salts of potassium, calcium, magnesium, iron, copper, manganese, molybdenum, boron and hydrophilic/lipophilic active ingredients to form a Wsi/O/W emulsion, and further comprising adding to the Wsi/O/W emulsion one or more of surface active agents, additives, binding agents, thickening agents, anti-foaming agents, aromatics, colorants, and/or flavorings.

21. The method of preparing an emulsion wherein the O/W emulsion of claim 19 is further emulsified into oil comprising one or more active ingredients selected from the group consisting of zinc oxide, calcium borate, manganese carbonate, magnesium carbonate, magnesium hydroxide and ammonium molybdate to form a O/W/O emulsion, and further comprising adding to the O/W/O emulsion surface one or more of active agents, additives, binding agents, thickening agents, anti-foaming agents, aromatics, colorants, and/or flavorings.

* * * * *